United States Patent
Rizo

(10) Patent No.: US 11,723,526 B2
(45) Date of Patent: Aug. 15, 2023

(54) DEVICE AND METHOD FOR OBSERVING AN OBJECT, TAKING INTO CONSIDERATION THE DISTANCE BETWEEN THE DEVICE AND THE OBJECT

(71) Applicants: COMMISSARIAT A L'ENERGIE ATOMIQUE ET AUX ENERGIES ALTERNATIVES, Paris (FR); FLUOPTICS, Grenoble (FR)

(72) Inventor: Philippe Rizo, La Tronche (FR)

(73) Assignees: COMMISSARIAT A L'ENERGIE ATOMIQUE ET AUX ENERGIES ALTERNATIVES, Paris (FR); FLUOPTICS, Grenoble (FR)

( * ) Notice: Subject to any disclaimer, the term of this patent is extended or adjusted under 35 U.S.C. 154(b) by 392 days.

(21) Appl. No.: 15/573,372

(22) PCT Filed: May 11, 2016

(86) PCT No.: PCT/FR2016/051115
§ 371 (c)(1),
(2) Date: Nov. 10, 2017

(87) PCT Pub. No.: WO2016/181077
PCT Pub. Date: Nov. 17, 2016

(65) Prior Publication Data
US 2018/0132708 A1    May 17, 2018

(30) Foreign Application Priority Data

May 12, 2015   (FR) ...................................... 1554259

(51) Int. Cl.
*A61B 1/06*    (2006.01)
*A61B 1/00*    (2006.01)
(Continued)

(52) U.S. Cl.
CPC ........ *A61B 1/0669* (2013.01); *A61B 1/00165* (2013.01); *A61B 1/00186* (2013.01);
(Continued)

(58) Field of Classification Search
CPC ... A61B 1/0669; A61B 1/00165; A61B 1/045; A61B 1/0607; A61B 1/3132; A61B 1/07;
(Continued)

(56) References Cited

U.S. PATENT DOCUMENTS 4,419,689 A  *  12/1983  Russell .................. G09G 1/285
                                                         348/701
4,638,800 A  *   1/1987  Michel ................. A61B 18/201
                                                          606/10
(Continued)

FOREIGN PATENT DOCUMENTS

EP    1 167 951 A1    1/2002
EP    2 020 202 A2    2/2009
(Continued)

OTHER PUBLICATIONS

International Search Report dated Sep. 6, 2016 in PCT/FR2016/051115.

*Primary Examiner* — Joel Lamprecht
*Assistant Examiner* — Amy Shafqat
(74) *Attorney, Agent, or Firm* — Oblon, McClelland, Maier & Neustadt, L.L.P.

(57) ABSTRACT

A device that can be used for in vivo fluorescence measurements by endoscopy or laparoscopy, including: an excitation light source illuminating an object, for example biological tissue, and inducing emission of emission light by the examined object, the emission light is, for example, a fluorescence light; a telemetry sensor emitting a telemetry light beam towards the object; a projector element to project the excitation beam and the telemetry beam directly on the
(Continued)

object. The telemetry sensor can estimate a distance between the projector element and the object, which distance makes it possible to modulate intensity of the excitation light emitted by the object. When the object is biological tissue, this makes it possible to comply with illumination thresholds of biological tissue and to maintain an illumination of constant intensity. The projector element can be included at the end of a laparoscope or of an endoscope.

25 Claims, 10 Drawing Sheets

(51) Int. Cl.
    *A61B 1/04*             (2006.01)
    *A61B 1/07*             (2006.01)
    *A61B 1/045*           (2006.01)
    *A61B 1/313*           (2006.01)
    *H04N 23/56*          (2023.01)
    *H04N 23/50*          (2023.01)
    *H04N 7/18*            (2006.01)

(52) U.S. Cl.
    CPC .............. *A61B 1/042* (2013.01); *A61B 1/043* (2013.01); *A61B 1/045* (2013.01); *A61B 1/0607* (2013.01); *A61B 1/07* (2013.01); *A61B 1/3132* (2013.01); *H04N 7/183* (2013.01); *H04N 23/555* (2023.01); *H04N 23/56* (2023.01)

(58) Field of Classification Search
    CPC ..... A61B 1/043; A61B 1/042; A61B 1/00186; H04N 2005/2255; H04N 7/183; H04N 5/2256
    See application file for complete search history.

(56) References Cited

U.S. PATENT DOCUMENTS

| | | | | |
|---|---|---|---|---|
| 5,928,222 | A * | 7/1999 | Kleinerman | G01J 5/0818 606/16 |
| 6,178,346 | B1 * | 1/2001 | Amundson | A61B 5/0086 348/77 |
| 6,280,378 | B1 * | 8/2001 | Kazuhiro | A61B 1/0638 348/65 |
| 7,184,614 | B2 * | 2/2007 | Slatkine | A61B 18/20 359/599 |
| 8,435,235 | B2 * | 5/2013 | Stevens | G02B 6/06 606/15 |
| 8,606,350 | B2 | 12/2013 | Ishihara | |
| 2001/0056238 | A1 | 12/2001 | Tsujita | |
| 2002/0139920 | A1 * | 10/2002 | Seibel | G01S 17/88 250/208.1 |
| 2009/0036743 | A1 | 2/2009 | Yabe et al. | |
| 2010/0157039 | A1 | 6/2010 | Sugai | |
| 2012/0249764 | A1 * | 10/2012 | Kuon | A61B 1/05 348/67 |
| 2014/0171764 | A1 * | 6/2014 | Kim | A61B 1/043 600/317 |
| 2015/0161802 | A1 * | 6/2015 | Christiansen | A61B 90/94 348/74 |
| 2016/0151055 | A1 * | 6/2016 | Leblond | A61B 5/14546 600/317 |
| 2017/0074652 | A1 * | 3/2017 | Send | G06F 3/0304 |

FOREIGN PATENT DOCUMENTS

EP          2 446 809 A1     5/2012
JP          2011-227132     11/2011

* cited by examiner

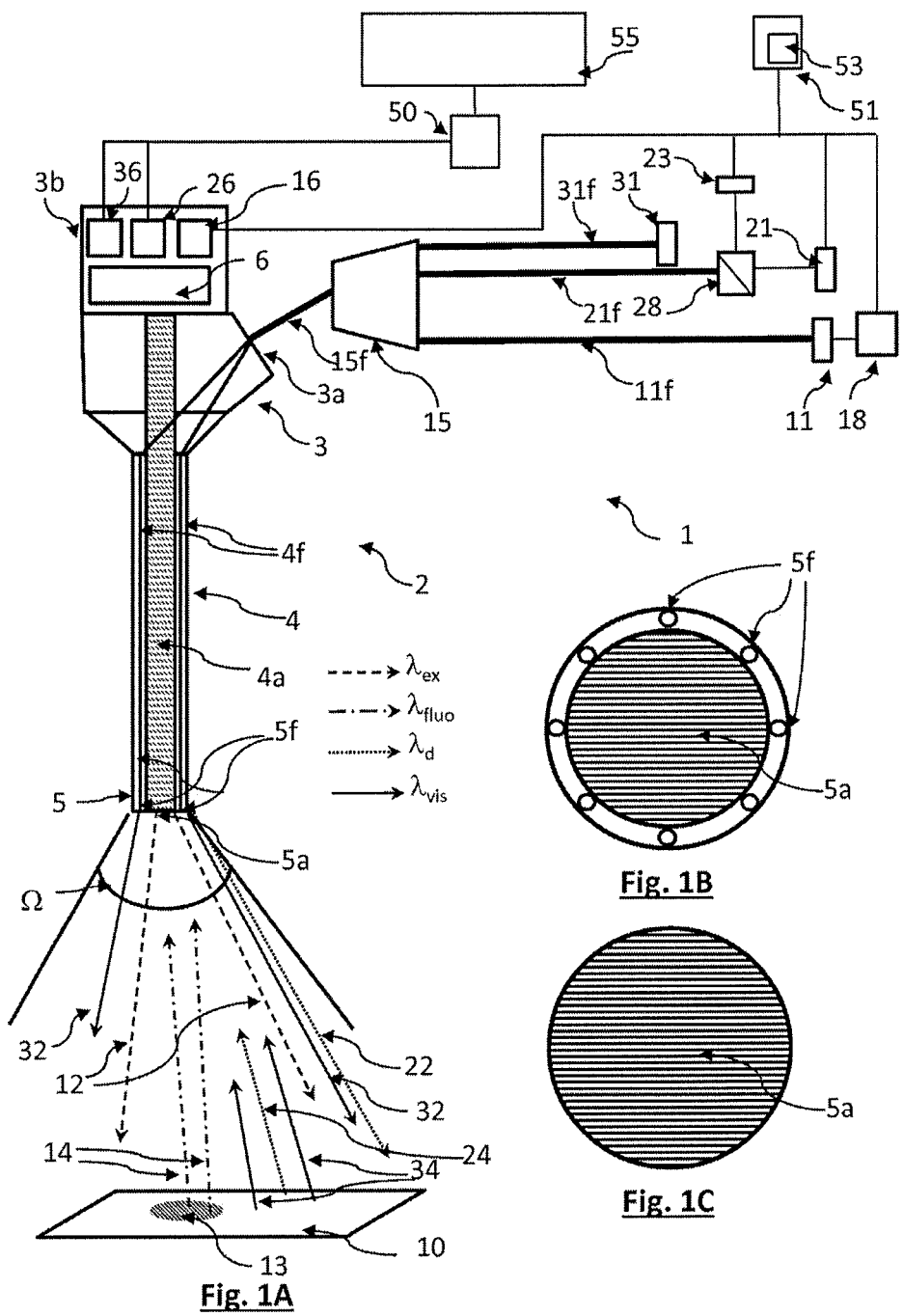

DEVICE AND METHOD FOR OBSERVING AN OBJECT, TAKING INTO CONSIDERATION THE DISTANCE BETWEEN THE DEVICE AND THE OBJECT

TECHNICAL FIELD

The field of the invention is the field of imaging of objects, in particular using endoscopic or laparoscopic light guides. The objects may in particular be bodily tissues. The imaging may be fluorescence imaging for diagnosing and tracking the evolution of pathologies or treatments.

PRIOR ART

Fluorescence imaging is a technique allowing fluorescent markers to be located in an animal or human body. One of its applications is the location of fluorescent markers, or fluorophores, the latter targeting cells of interest, for example cancerous cells. The protocol consists in injecting these markers into the organism before a surgical intervention, so that, during the intervention, the practitioner is able to see the cancerous cells via a fluorescence image. Because it allows an image indicating the location of various cancerous zones to be acquired, preoperative fluorescence imaging allows information that was previously unavailable to the practitioner to be obtained and is a useful complement, or even an alternative, to the use of radioactive tracers. Another application is as an aid in interventions in cardio-vascular surgery, in surgery on the lymphatic system, or in hepatic surgery, in which fluorescence imaging allows visual inspection of drainage, of perfusion, or of the distribution of blood vessels.

The principle of fluorescence imaging is to illuminate a field of observation using a light source in an excitation spectral band of the fluorophores. Under the effect of this illumination, the fluorophores emit fluorescence radiation, in a fluorescence spectral band. This radiation may be captured by a fluorescence video camera, so as to form a fluorescence image in which various fluorescent zones appear. It is then possible to acquire a visible image of the observed field, and to superpose the fluorescence image on this visible image.

One way in which fluorescence imaging may be applied is via an endoscopic or laparoscopic technique, allowing fluorescence images of a biological tissue in the interior of an organism to be acquired using a minimally invasive access technique. Document US20130184591 for example describes a laparoscope comprising a distal end, which is intended to be inserted into an organism, in proximity to the examined tissue, and a proximal end, which is intended to remain outside of the organism.

The proximal end is connected to a light source that produces an excitation beam that allows fluorescence light to be emitted by fluorophores that are potentially present in the tissue, markers having being introduced beforehand into the organism to be examined. This end is also connected to a visible-light source. The laparoscope moreover comprises, at its proximal end, a visible-image sensor and a fluorescence-image sensor. Spectrally splitting optical means allow the visible light reflected by the biological tissue and the fluorescence light to be directed toward the visible-image sensor and the fluorescence-image sensor, respectively.

Transmission of the fluorescence light and the visible light from the examined tissue to the proximal end requires a collecting optical system, placed at the distal end, in order to collect optical signals in a certain field of observation. This transmission moreover requires a transmitting optical system, or optical relay, in order to transmit the visible and fluorescence light to their respective image sensors, which are placed at the proximal end.

Because of the small aperture of these optical systems, the amount of fluorescence signal reaching the proximal end is small. It may be increased by increasing the intensity of the excitation beam. However, increasing the excitation-light signal risks drying or burning the examined tissue. In particular, when the excitation beam is produced by a laser source, it is necessary to meet regulatory requirements, for example the international standard IEC 60825-1, which relates to the safety of laser products. The device described in this document allows the exposure of the tissue to be controlled via analysis of the signals detected by the image sensors housed in the proximal end of the laparoscope.

Document EP1167951 describes an endoscope for analyzing the fluorescence of a sample. This document describes how, on the basis of a visible image of the sample or of a fluorescence image of the latter, and more precisely on the basis of the number of pixels the brightness of which exceeds a certain threshold, it is possible to determine that a certain critical distance between one end of the endoscope and the surface of the sample has been breached. The intensity of an excitation beam may be adjusted accordingly. However, the detection of the breach of the critical distance depends on reflective and/or backscattering optical properties of the sample.

Document US 20100157039 describes an endoscope for analyzing the fluorescence of a sample, allowing a distance between an end of the endoscope and a surface of the sample to be measured. The distance is determined on the basis of an infrared image of the sample, the surface of the latter being scanned by an infrared light beam, the scan taking the form of a spiral.

Document EP 2020202 describes an endoscope for analyzing the fluorescence of a sample. On the basis of an evaluation of the breach of a critical distance between an end of the endoscope and an analyzed surface of the sample, an auxiliary light source may be modulated, so as to prevent nonuniformity in the illumination of the sample. The breach of the critical distance is evaluated on the basis of a luminance of a fluorescence image acquired by the endoscope.

However, control of the exposure of tissues, or determination of a distance, with an image sensor lacks precision, and may in particular depend too strongly on the reflective or backscattering optical properties of the sample. The inventors have designed a device and a method for observing an object, in particular a bodily tissue, and in particular via an endoscopic or laparoscopic technique, allowing a fluorescence image to be acquired while ensuring that the illumination of the examined tissue meets the requirements in force with respect to the integrity of these tissues, guaranteeing safety in use.

SUMMARY OF THE INVENTION

One subject of the invention is a device for observing an object, including:
- an excitation-light source able to produce, in an excitation spectral band, an excitation beam that propagates toward said object;
- an emission-image sensor that is able to collect emission light emitted, in an emission spectral band, by said object under the effect of said excitation beam, the emission-image sensor being able to acquire an emission image on the basis of the collected emission light; and a distance sensor including a rangefinding-light source that is able to produce, in a rangefinding spectral band, a rangefinding beam that propagates toward the object, the distance sensor also including a rangefinding-light sensor that is able to detect rangefinding light reflected by the object, the device being characterized in that it includes:

a projecting element that is configured to project said excitation beam and said rangefinding beam toward the object, in a projection solid angle, the distance sensor being able to measure a distance between said projecting element and said object; and a modulator that is configured to modulate an intensity of the excitation beam depending on said distance measured by the distance sensor.

The device may in particular include a light guide extending between a proximal end and a distal end, the light guide being able to transmit:

the excitation beam and the rangefinding beam from said proximal end to said distal end; and the emission light and said rangefinding light reflected by the object from said distal end to said proximal end, the distal end of said light guide including said projecting element.

In particular, the distal end is intended to be inserted into the body of a human or of an animal, so as to be able to be placed facing the object to be examined. The object to be examined is in particular a biological tissue and in particular a bodily tissue.

The light guide may be a laparoscope or an endoscope.

The light guide may include, at its distal end, an optical system that is able to collect the emission light and rangefinding light coming from the object, so as to direct said light toward the proximal end of the light guide. This optical system may in particular include an objective or a lens. This optical system defines an observation solid angle, the intersection of which with the object forms the observed field.

This optical system may also be able to direct said excitation beam and said rangefinding beam toward said object, said optical system then forming the projecting element.

The light guide may include at least one transmitting optical fiber extending between the proximal end and the distal end of the light guide so as to guide the excitation beam and the rangefinding beam between said proximal end and said distal end, the end of each transmitting optical fiber at said distal end forming the projecting element.

Preferably, the projecting element directs the excitation beam and the rangefinding beam into the same projection solid angle.

The distance sensor is able to measure a duration between the emission of the rangefinding beam by the rangefinding-light source and the detection, by the rangefinding-light sensor, of the rangefinding light reflected by the object.

The projection of the excitation beam and of the rangefinding beam defines an illuminated field on the object. Preferably, the illuminated field is identical to or inscribed in the observed field.

The light guide may include a spectral splitter that is able to direct:

the emission light toward the emission-image sensor; and
the rangefinding light reflected by the object toward the rangefinding-light sensor.

The spectral splitter, the emission-image sensor and the rangefinding-light sensor may be housed at the proximal end of the light guide, for example in a detecting module located at this proximal end.

The device may include:

a visible-light source that is able to emit, in a visible spectral band, a visible-light beam toward said object; and a visible-image sensor that is able to collect visible light reflected by the object under the effect of illumination by said visible-light beam, the visible-image sensor being able to acquire a visible image on the basis of the collected visible light;

the light guide then being able to transmit:

said visible-light beam from the proximal end to the distal end;

and said visible light reflected by the object from the distal end to the proximal end.

The visible-image sensor may be housed at the proximal end of the light guide, for example in the detecting module integrated into this proximal end.

The rangefinding-light source and the excitation-light source may be one and the same.

In this case, the measurement of distance is carried out using the propagation of the excitation light from the excitation-light source to the object and the propagation of the excitation light reflected by the object between the latter and the rangefinding-light sensor.

The rangefinding spectral band may be different from the excitation spectral band and from the emission spectral band, or even from the visible spectral band.

The distance sensor may include:

a distributor that is able to redirect a portion of said rangefinding beam emitted by the rangefinding source toward a triggering photodetector, the latter being able to detect said rangefinding-beam portion redirected by said distributor; and a rangefinding processor that is able to determine a distance travelled by the rangefinding beam between the rangefinding-light source and the rangefinding sensor on the basis of a trigger time at which the triggering photodetector detects said rangefinding beam and of an end time at which said rangefinding-light sensor detects said rangefinding light reflected by the object, the rangefinding processor being able to determine said distance between the projecting element and the object on the basis of the distance travelled by the rangefinding beam.

The triggering photodetector and the rangefinding processor may be included in the light guide.

Another subject of the invention is a method for observing an object, including the following steps:

illuminating an object with a rangefinding-light beam emitted, in a rangefinding spectral band, by a rangefinding-light source, the illuminating beam being projected onto the object by a projecting element defining a projection solid angle;

detecting rangefinding light reflected, in said rangefinding spectral band, by the object;

measuring a distance between the projecting element and the object, on the basis of said detected rangefinding light and in particular on the basis of a duration between the emission of the rangefinding beam and the detection of the rangefinding light reflected by the object;

illuminating said object using an excitation beam emitted, in an excitation spectral band, by an excitation-light source, said excitation beam being projected onto the object by said projecting element in said projection solid angle;

detecting emission light with an emission-image sensor, said emission light being emitted by the object under the effect of said illumination by the excitation beam; and acquiring an emission image with said emission-image sensor on the basis of said detected emission light, the method being characterized in that it also includes:

modulating an intensity of the excitation beam depending on the measured distance.

The intensity of the excitation beam may be modulated by modulating a signal controlling the excitation-light source or by placing an attenuator intermediate between the excitation-light source and the object.

According to one embodiment:

the excitation beam and the rangefinding-light beam are transmitted to the object by a light guide a distal end of which, comprising the projecting element, is placed facing the object, the light guide also ensuring the transmission of said emission light emitted by the object and said rangefinding light reflected by the object to the emission-image sensor and the rangefinding-light sensor, respectively.

The emission-image sensor and the rangefinding-light sensor may in particular be placed at the proximal end of the light guide, for example in a detecting module integrated into this proximal end.

The emission light emitted by the object and the rangefinding light reflected by the object may be collected by an optical system that is located at the distal end of the light guide, before being redirected toward the emission-image sensor and the rangefinding-light sensor, respectively. The optical system defines an observed field on the object, such as defined above.

This optical system, which may in particular include an objective or a lens, defines an observed field on the object, corresponding to an area of the object from which the emission light and rangefinding light collected by the optical system come.

According to one embodiment, the excitation beam and the rangefinding beam are projected onto the object by said optical system, the latter then forming said projecting element.

According to one embodiment, the excitation beam and the rangefinding beam are projected onto the object by at least one optical fiber extending between the proximal end and the distal end of the light guide, the end of each optical fiber at said distal end forming the projecting element.

According to one embodiment, the emission light is fluorescence light in an emission spectral band, or fluorescence spectral band, that is different from the excitation spectral band.

According to one embodiment, the emission light corresponds to reflection or of the excitation beam from the object and/or to backscatter of the excitation beam in the object. The emission spectral band therefore corresponds to the excitation spectral band.

According to one embodiment, the method also includes:

illuminating, in particular through the light guide, the object with a visible-light beam produced, in a visible spectral band, by a visible-light source; and acquiring a visible image of the object using a visible-image sensor, the latter detecting visible light reflected by the object, in particular through the light guide.

According to one embodiment, the rangefinding-light source and the excitation-light source are one and the same, the rangefinding spectral band then corresponding to the excitation spectral band.

According to one embodiment, the rangefinding spectral band is different from the excitation spectral band and from the emission spectral band, or even from the visible spectral band.

Another subject of the invention is a device including:

a distance sensor including a rangefinding-light source that is able to emit, in a rangefinding spectral band, a rangefinding beam that propagates toward the object, the distance sensor also including a rangefinding-light sensor that is able to detect rangefinding light reflected by the object, the device being characterized in that it includes:

a light guide extending between a proximal end and a distal end, the light guide being able to transmit the rangefinding beam from said proximal end to said distal end and said rangefinding light reflected by the object from the distal end to said proximal end, the distal end of said light guide including a projecting element for projecting said rangefinding beam toward the object in a projection solid angle, the distance sensor being able to measure a distance between said projecting element and said object.

In particular, the distal end is intended to be inserted into the body of a human or of an animal, so as to be able to in particular be placed facing the object to be examined. The object to be examined is in particular a biological tissue and in particular a bodily tissue. The light guide may in particular be a laparoscope or an endoscope.

The light guide may include, at its distal end, an optical system that is able to collect the rangefinding light coming from the object, so as to direct it toward the proximal end of the light guide. This optical system may in particular include an objective or a lens. This optical system defines an observation solid angle, the intersection of which with the object forms the observed field.

Preferably, the surface of the object is divided into surface elements. The distance sensor is then able to measure a distance between said projecting element and each surface element. The distance sensor may in particular comprise a matrix-array photodetector including a plurality of pixels, and is able to determine a distance between each pixel and each surface element to which said pixel is optically coupled.

According to one embodiment, the device comprises a processor that is connected to the distance sensor and that is able to establish a three-dimensional map of the observed field.

The rangefinding-light sensor may in particular be placed at the proximal end of the light guide, for example in a detecting module included in this proximal end.

The device may include:

an excitation-light source able to produce, in an excitation spectral band, an excitation beam that propagates toward an object; and an emission-image sensor that is able to collect emission light emitted, in an emission spectral band, by said object under the effect of said excitation beam, the emission-image sensor being able to acquire an emission image on the basis of the collected emission light, the light guide being able to transmit said excitation beam to the object and to transmit said emission light reflected by the object to said emission-image sensor.

The latter may in particular be placed in the light guide, in particular at its proximal end.

Another subject of the invention is a method including the following steps:

illuminating an object with a rangefinding-light beam produced, in a rangefinding spectral band, by a rangefinding-light source, the rangefinding beam being projected onto the object by a projecting element defining a projection solid angle;

detecting rangefinding light reflected, in said rangefinding spectral band, by the object, with a rangefinding-light sensor;

measuring a distance between the projecting element and the object, on the basis of said detected rangefinding light, the method being characterized in that:

the rangefinding beam is transmitted to the object by a light guide a distal end of which, comprising the projecting element, is placed facing the object, the light guide also ensuring the transmission of said rangefinding light reflected by the object to the rangefinding-light sensor.

The rangefinding light reflected by the object may be collected by an optical system located at the distal end of the light guide, before being redirected toward the rangefinding-light sensor. The optical system defines an observed field on the object, such as defined above.

According to one embodiment, the surface of the object is divided into surface elements. The method then includes a step of measuring a distance between said projecting element and each surface element. In this embodiment, the distance sensor may in particular comprise a matrix-array photodetector. The matrix-array photodetector includes a plurality of pixels so as to determine a distance separating each pixel from the surface element to which said pixel is optically coupled.

In this embodiment, the method may include producing a three-dimensional map of the observed field, on the basis of the measured distance corresponding to each surface element.

The method may include the following steps:

illuminating said object using an excitation beam emitted, in an excitation spectral band, by an excitation-light source, said excitation beam being projected onto the object by said projecting element, in said projection solid angle;

detecting emission light with an emission-image sensor, said emission light being emitted by the object under the effect of said illumination by the excitation beam; and acquiring an emission image with said emission-image sensor on the basis of said detected emission light.

According to this variant, the excitation beam may be transmitted to the object by said light guide, the latter also ensuring the transmission of said emission light emitted by the object to the emission-image sensor.

FIGURES

FIG. 1A shows a first embodiment of a device according to the invention.

FIGS. 1B and 1C show a detail of two different variants of the distal end of the light guide.

DESCRIPTION OF PARTICULAR EMBODIMENTS

Figure 1D:
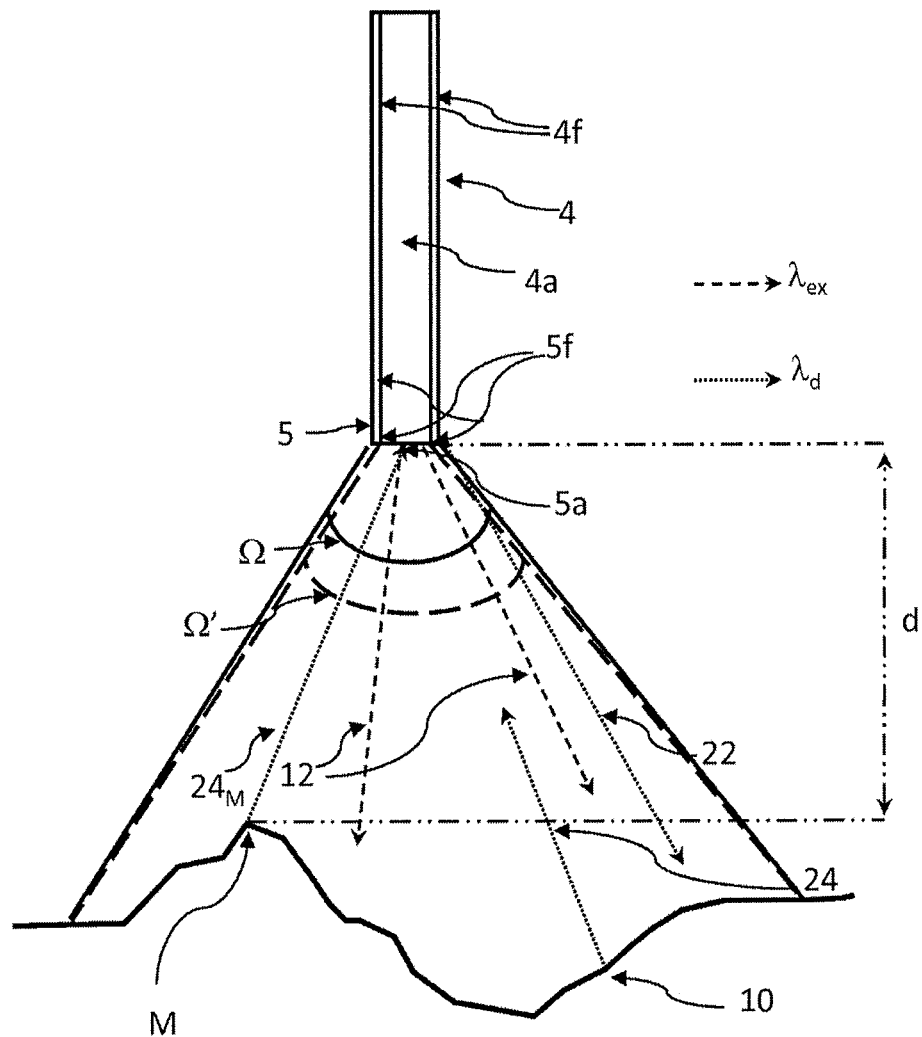
FIG. 1D shows a detail of the distal end of the light guide and of the object.

FIG. 1 shows a device 1 according to a first embodiment. The device includes an excitation-light source 11 that is able to emit, in an excitation spectral band $\lambda_{ex}$, an excitation-light beam 12, so as to illuminate an object 10. The object 10 is for example a biological tissue exposed to the device 1 during a laparoscopic or endoscopic intervention.

The expression spectral band designates all of the wavelengths comprised in a set interval, between a minimum wavelength and a maximum wavelength.

The excitation-light source 11 may be continuous, amplitude modulated, or pulsed.

The excitation-light source 11 is, in this example, a pulsed laser diode emitting at a wavelength $\lambda_{ex}$=750 nm. It may also be a light-emitting diode.

The light source may comprise an excitation filter that is able to block wavelengths outside of the excitation spectral band $\lambda_{ex}$.

The device includes a light guide 2 including a proximal end 3 and a distal end 5. The light guide allows the transmission of light between the proximal end 3 and the distal end 5 and vice versa.

This light guide is, in this example, a laparoscope. It may also be an endoscope. The proximal end 3 comprises an entrance window 3a that is able to receive light beams intended to be transmitted to the distal end 5. The proximal end also comprises a detecting module 3b, allowing light rays collected by the distal end 5 to be detected.

In this example, the excitation-light beam emitted by the light source 11 is transmitted by an excitation optical fiber 11f (or a plurality of excitation optical fibers), which convey the excitation beam between the excitation-light source 11 and an optical coupler 15. A coupling optical fiber 15f, or a plurality of coupling optical fibers 15f, convey the excitation beam 12 between the optical coupler 15 and the entrance optical window 3a. The latter includes an optical connector allowing the excitation beam to be transmitted to the light guide 2.

The light guide 2 includes a central segment 4 that extends between the proximal end 3 and the distal end 5, so as to transmit light between these two ends. In the example shown, the central segment 4 includes a plurality of transmitting optical fibers 4f that are intended to transmit the excitation-light beam 12 between the proximal end 3 and the distal end 5. The central segment 4 also includes a relaying optical element 4a (known per se) for example comprising relaying lenses and able to transfer light, and in particular an image, between the distal end 5 and the proximal end 3, and vice versa. The optical fibers 4f are for example distributed around the periphery of the relaying segment, the relaying optical element 4a being placed in the central portion of the central segment 4. Generally, the light guide 2 includes several tens or even hundred transmitting optical fibers 4f.

According to one variant, the central segment is flexible and includes a bundle of optical fibers. The diameter of the central segment is generally smaller than 1 or 2 cm.

The length of the central segment is for example comprised between 10 and 30 cm when the light guide is rigid, for example when it is a question of a laparoscope. In the case of an endoscope, the length of the guide may exceed 1 meter or even several meters.

The distal end 5 is intended to be inserted into the body of an animal or of a human. It includes a projecting element intended to project the excitation beam 12 onto the object 10. The light is emitted, from the projecting element, in an emission cone defining a projection solid angle Ω. The intersection of the emission cone with the object 10 corresponds to the illuminated field.

By projecting element, what is meant is an optical element allowing a beam of light to be projected onto the object, in an emission cone. It may in particular be a question of the end of one or more optical fibers or of an optical system such as a lens or objective.

In the example shown in FIG. 1A, the distal end 5f of each transmitting optical fiber 4f terminates level with the distal end 5 of the guide. The projecting element then consists of all of the distal ends 5f of all the transmitting optical fibers 4f. FIG. 1B shows the distal end 5 of the light guide corresponding to the configuration described in FIG. 1A.

The light guide is also able to transmit light collected by the distal end 5 to the proximal end 3, through the central segment 4. Thus, the distal end 5 includes a distal optical system 5a the function of which is to collect light rays originating from the observation field 10 located facing the distal end 5. Thus, the distal optical system 5a defines an observation solid angle ST the intersection of which with the surface of the object forms the observed field. The light collected at the distal end 5, by the distal optical system 5a, may be transferred by the relaying optical element 4a to a detecting module 3b, which is integrated into the proximal end 3. The function of the detecting module 3b is to detect light collected at the distal end 5 and transmitted to the proximal end 3.

Under the effect of the illumination by the excitation beam 12, the object 10 emits emission light 14 in an emission spectral band $\lambda_{em}$. The emission light 14 may be a portion of the illuminating beam 12, this portion being reflected or backscattered by the object 10, the emission spectral band $\lambda_{em}$ then being analogous to the excitation spectral band $\lambda_{ex}$. In the example shown in FIG. 1A, the emission light 14 is fluorescence light, emitted by the object, at a fluorescence wavelength $\lambda_{fluo}$ that is different from the excitation wavelength $\lambda_{ex}$.

The object 10 includes one or more endogenous or exogenous fluorophores. In the case where the fluorophores are endogenous, autofluorescence is spoken of. Exogenous fluorophores are injected beforehand into the object, so as to specifically fix to targets, for example cancerous cells. Each fluorophore is able to emit fluorescence radiation 14, in the fluorescence spectral band $\lambda_{fluo}$, when it is illuminated by excitation light 12, in an excitation spectral band $\lambda_{ex}$. For example, when the fluorophore used is indocyanine green (ICG), the excitation spectral band may be comprised between 750 nm and 800 nm, the fluorescence spectral band being comprised between 820 nm and 870 nm.

Thus, under the effect of the excitation beam transmitted by the distal end 5 of the guide 2, the object may emit fluorescence light 14. In the example shown, the object 10 includes a fluorescent zone 13 that is able to emit such fluorescence light 14. Some of the latter is collected by the distal optical system 5a, then transferred, through the relaying segment 4, to a detecting module 3b that is included in the proximal end 3.

The detecting module 3b includes a spectral splitter 6 that is able to direct an incident light beam in a given direction depending on its spectral band. The spectral splitter 6 directs the emission light 14 to an emission-image sensor 16. The emission-image sensor is able to form an image of the emission light 14 produced by the object 10 under the effect of illumination by the excitation beam 12 emanating from the distal end 5. This image sensor 16 will be detailed below.

A processor 50 is able to process the emission images formed by the image sensor 16. It is for example a question of a microprocessor integrated into a desktop computer. In particular, the processor is a microprocessor connected to a programmable memory in which a sequence of instructions for carrying out the image-processing operations is stored. These operations are for example the removal of certain background noises, coloring or superposition with other images, as described below.

A screen 55, which is connected to the processor, allows the images collected by the image sensor 16 and processed by the microprocessor 50 to be viewed.

According to one variant, which is shown in FIG. 1C, the central segment 4 includes no transmitting optical fibers 4f, the excitation beam being transmitted by the relaying optical element 4a between the proximal end 3 and the proximal end 5. In such a variant, the distal optical system 5a plays the role of the element projecting the excitation beam onto the object 10, defining a projection solid angle Ω. It will be understood that in this variant, the projection solid angle is equal to the observation solid angle Ω', the illuminated and observed fields being identical.

Distance Measurement

The device also includes a distance sensor. The latter is based on the well-known principle of optical time-of-flight rangefinding, which consists in evaluating the duration between the emission of a light pulse and the detection of this pulse. This duration is representative of the distance travelled by the light forming the pulse between its emission and its detection.

The distance sensor comprises a light source 21, called the rangefinding-light source, which is able to emit a rangefinding-light beam 22 in a rangefinding spectral band $\lambda_d$. The light source 21 is preferably pulsed. It emits light pulses, or rangefinding pulses, at a pulse frequency that may be comprised between 1 Hz and 100 Hz or even 1 kHz. In this example, the light source 21 is a pulsed laser diode emitting at a wavelength $\lambda_d$=950 nm. It is controlled by a rangefinding processor 51. The rangefinding spectral band $\lambda_d$ may be located below 400 nm or above 900 nm, so as to be located neither in the visible spectrum, nor in an emission spectral band (and in particular a fluorescence spectral band). Thus, the rangefinding light is not detected by the visible- or emission-image sensors.

The rangefinding-light beam 22 passes through a light distributor 28 that is able to direct a first portion of the rangefinding beam toward the light guide 2, through a rangefinding optical fiber 21f, or a plurality of rangefinding optical fibers 21f. Each rangefinding fiber is linked to the light guide 2 by the optical coupler 15, which leads onto the coupling optical fiber 15*f*. This optical fiber allows the excitation beam 12 and the rangefinding beam 22 to be transmitted to the entrance window 3*a* of the light guide. The optical coupler 15 allows the rangefinding and excitation beams to be guided, in the same optical fiber or in the same bundle of optical fibers, to the light guide 2.

A second portion of the rangefinding beam 22 is directed toward a triggering photodetector 23. Preferably, the second portion of the rangefinding beam is smaller than the first portion, and represents no more than 20% or 10% of the beam emitted by the rangefinding source 21.

The triggering photodetector 23 is for example a photodiode, for example an avalanche photodiode the passband of which is matched to the rangefinding spectral band $\lambda_d$.

Figure 2:
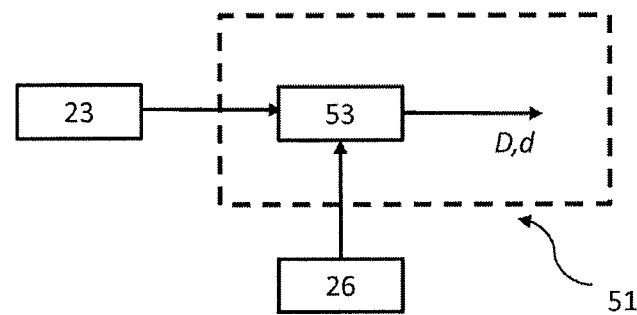
FIG. 2 shows a detail of the structure of the distance sensor.

As shown in FIG. 2, the detection of a pulse by the triggering photodetector 23 causes, in the rangefinding processor 51, the activation of the incrementation of a rangefinding counter 53 at a clock frequency, the latter for example being 20 MHz. This rangefinding counter is included in the rangefinding processor.

Just like the excitation beam 12, the rangefinding beam 22 is directed toward the object 10 in the light guide 2 and through the entrance window 3*a*. It then reaches the distal end 5 by being transmitted by the transmitting fibers 4*f*, from the end of which it is emitted in the direction of the object 10 in an emission cone that is identical, or substantially similar, to the emission cone of the excitation beam 12, of projection solid angle $\Omega$.

In the variant shown in FIG. 1C, the rangefinding beam 22 is transmitted to the distal end 5 by the optical relay 4*a* and, just like the excitation beam 12, is projected onto the object by the distal optical system 5*a*.

Because of the difference in the wavelength of the excitation beam 12 and the rangefinding beam 22, differences may appear between the emission cone of the excitation beam and the emission cone of the rangefinding beam. However, these differences may be neglected and these two emission cones may be considered to form only a single cone defining the same projection solid angle $\Omega$. This is moreover one noteworthy advantage of the invention.

According to one variant, the excitation optical fiber 11*f* and the rangefinding optical fiber 21*f* extend as far as to the optical window 3*a*. However, it is preferable to place an optical coupler 15 between, on the one hand, the rangefinding-light source 12 and the excitation-light source 11 and, on the other hand, the light guide 2. The function of the optical coupler is to couple the excitation optical fiber and the rangefinding optical fiber to a coupling optical fiber, the latter being able to transmit the two beams to the light guide. Thus, the illumination of the object, by either one of these beams, is similar, both in terms of the extent and in terms of the spatial distribution of the illumination on the object.

Some of the rangefinding beam 22 reaches the object 10 and is reflected by the latter, thus forming reflected rangefinding light 24. Some of this reflected light 24 is collected by the distal optical system 5*a*, then redirected by the optical relay 4*a* to the detecting module 3*b*, at the proximal end 3. In the detecting module 3*b*, the spectral splitter 6 directs the reflected rangefinding light 24 to a rangefinding-light sensor 26. This light sensor may for example be a photodiode, and in particular an avalanche photodiode, analogously to the triggering photodetector 23 described above.

Since the emission of the rangefinding-light beam 22 is pulsed, the same goes for the detection of the rangefinding light 24 reflected by the object. When a pulse is detected by the rangefinding-light sensor 26, the incrementation of the rangefinding counter 53 is stopped. The value of the counter, i.e. the number of increments between its activation, which is triggered by the triggering photodetector 23, and its stoppage, which is triggered by the rangefinding-light sensor 26, allows a distance D travelled by the rangefinding pulse 22, between the rangefinding-light source 21 and the rangefinding photodetector 26, to be measured, as shown in FIG. 2. This measurement may be carried out, by the rangefinding processor 51, by implementing a time-to-digital converter (TDC). This processer may in particular be incorporated into a rangefinding microcontroller.

The distance d between the distal end 5 of the guide, and more precisely of the projecting element 5*f*, and the object 10 is estimated by the rangefinding processor 51, on the basis of the dimensions of the light guide, and in particular the distances travelled by the rangefinding light between the rangefinding source 21 and the distal end 5 and between the distal end 5 and the rangefinding sensor 26, respectively. This estimation may be achieved on the basis of a calibration, allowing this distance d to be estimated depending on the measurement taken by the distance sensor. An example of calibration is presented in FIG. 10.

It is also possible to measure a distance $\delta$ travelled by the excitation beam 22 between the excitation source 21 and the object 10.

On the basis of the estimation of the distance d between the projecting element 5*f* and the object 10, the rangefinding processor 51 addresses a control signal to a modulator 18 in order to modulate the intensity of the excitation beam emitted by the excitation source 11, so that the power delivered by the excitation beam 12 to the object is lower than a maximum permitted power Pmax, this in order to avoid any risk of lesion of the object by the excitation beam, in particular when the object is a bodily tissue. For example, at $\lambda_{ex}=750$ nm, the maximum power per unit area is 0.25 W/cm$^2$. This adjustment of intensity is based on the smallest distance d, in the field of observation, between the object and the distal end 5 of the excitation guide. To each distance d corresponds a maximum allowable power per unit area Pmax$_d$, this maximum power possibly being determined experimentally, then tabulated in a memory.

The intensity of the beam may be adjusted by modulating a signal controlling the excitation-light source. It may also be achieved by placing attenuators, or optical densities, on the path of the excitation beam.

The similarity of the optical paths of the rangefinding beam 22 and the excitation beam 12 in the light guide 2 will be noted. These two beams are projected by the projecting element 5*f* (or 5*a* where appropriate) onto the object in the same projection solid angle $\Omega$. Thus, and this is an important element of the invention, the surface of the object illuminated by the excitation beam 12 corresponds to the surface illuminated by the rangefinding beam 22.

Hence, the measured distance d depends on the point M of the object 10 closest to the distal end 5. This property is particularly useful when the object 10 is not flat, and is liable to include, in a given observed field, zones that are closer to and zones that are further away from the distal end 5. Because the rangefinding beam 22 is distributed in the same solid angle $\Omega$ as the excitation beam, the measured distance is the smallest distance, in the observed field, between the object and the distal end 5 (or between the object and the excitation source 11). The power of the excitation beam is therefore adjusted on the basis of the point of the field observed and that, receiving the excitation beam, is closest to the distal end 5.

This aspect is illustrated in FIG. 1D, which shows an object the surface of which is not flat. This surface is illuminated by the excitation beam 12 and by the rangefinding beam 22, via the projecting element 5f, with the same projection solid angle Ω. The distal optical system 5a collects, in the same observation solid angle Ω', the emission light 14 (in this case, fluorescence light) and the rangefinding light 24 that is reflected by the object. The point M corresponds to the point of the surface of the object closest to the distal end 5. Following the illumination of the surface of the object by the rangefinding beam 22, the point M is the first point of the surface illuminated. Thus, the first rangefinding ray reflected by the object is the ray $24_M$. The latter is collected by the distal optical system 5a, then redirected toward the detecting module 3b, in order to be detected by the rangefinding photodetector 26. The rangefinding counter 53 is then stopped. The measured distance D, which is representative of the optical path of the rangefinding beam between the rangefinding source 21 and the rangefinding photodetector 26, therefore depends on that point of the surface of the object which is closest to the projecting element located at the distal end 5 of the light guide 2, in the present case the point M. The same goes for the distanced determined, on the basis of D, between the distal end 5 and the object 10.

Whatever the embodiment, the projection solid angle Ω is preferably smaller than or equal to the observation solid angle Ω'. Advantageously, the projection solid angle Ω is identical to the observation solid angle Ω', such that the illuminated field $S_Ω$ corresponds to the observed field. Specifically, the distance measurement is carried out on the surface of the object located in the zone of overlap of the illuminated field and the observed field. The area of the illuminated field depends on the targeted application. In endoscopy, it is larger than 5 mm$^2$, or even than 1 cm$^2$, whereas in preoperative fluorescence imaging, it is larger than 5 cm$^2$ or even 10 cm$^2$.

In the example shown, the triggering of a pulse by the rangefinding-light source 21 is controlled by the rangefinding processor 51.

It is also possible, knowing this distance d, to modulate the excitation beam 12 such that the illumination delivers a constant power per unit area, called the setpoint power, to the point of the object 10 closest to the light guide, independently of the position of the distal end 5 with respect to the object 10. To do this, the modulator 18 adjusts the intensity of the excitation beam with respect to a reference distance $d_{ref}$ such that whatever the distance d between the distal end and the object, the power per unit area P delivered to the object is constant. For example, if $P_{ref}$ is the setpoint power, the intensity of the beam is modulated, the distance d being known, by a modulation function $f_d$ dependent on this distance, such that $f_d(P)=P_{ref}$.

Visible Image

The device may also include a visible-light source 31 that is able to direct visible light 32, in a visible spectral band $λ_{vis}$, toward the object 10, through a visible optical fiber 31f and the light guide 2.

The visible-light source 31 may in particular be a continuous-wave or pulsed white-light source. In this example, the visible-light source is a light-emitting diode emitting white light.

Some of the visible light is reflected by the object and is collected by the distal optical system 5a in order to be redirected toward the proximal end 3 of the light guide 2, and more precisely toward the detecting module 3b. The spectral splitter 6 directs the reflected visible light 34 toward a visible-image sensor 36, the latter forming a visible image $I_{vis}$.

The processor 50 is able to process the visible images $I_{vis}$ formed by the visible-image sensor 36, by applying image-processing operations. One processing operation is for example the superposition with an emission image generated by the emission-image sensor 16, the emission image being colored beforehand. The screen 55 allows the visible image and/or the image obtained following the superposition to be viewed.

It will be noted that the rangefinding-light source 21 may be triggered synchronously with the visible-light source 31, or asynchronously. When the rangefinding spectral band $λ_d$ includes wavelengths of the visible spectral band $λ_{vis}$, the rangefinding-light source 21 is triggered synchronously with the times at which the visible-light source 31 is turned off.

Detecting Module

Figure 3:
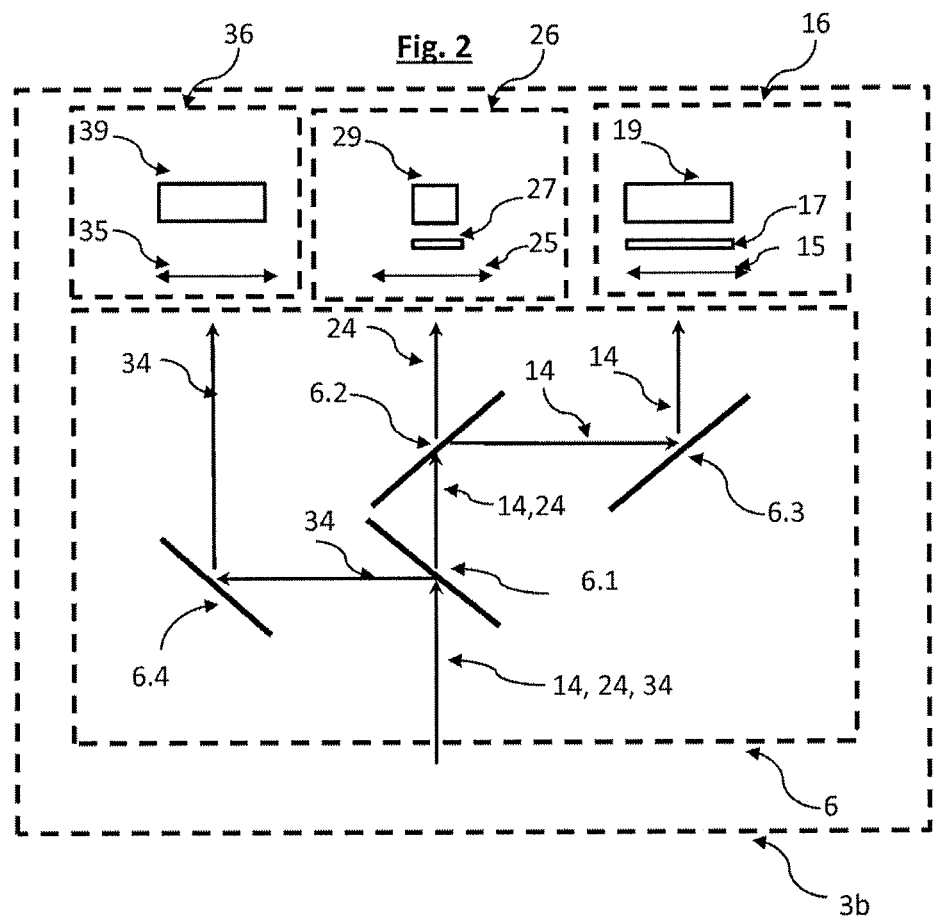
FIG. 3 shows a detail of the proximal end of the light guide.

FIG. 3 illustrates one example of a detecting module 3b forming part of the proximal end 3 of the light guide 2.

The aforementioned spectral splitter 6 is intended to redirect various light beams to a specific detector depending on their wavelength, using semi-reflective mirrors or dichroic filters that transmit the light in a given spectral band and reflect the light in another spectral band.

A first semi-reflective mirror 6.1 transmits the light in the emission spectral band $λ_{em}$ and the rangefinding spectral band $λ_d$. This first semi-reflective mirror reflects the light 34 in the visible spectral band $λ_{vis}$ toward a mirror 6.4, the latter reflecting the visible light toward the visible-image sensor 36. This image sensor comprises a matrix-array photodetector 39 that is coupled to a focusing optical system 35.

A second semi-reflective mirror 6.2 transmits the light in the rangefinding spectral band $λ_d$ toward a rangefinding-light sensor 26 and reflects the light in the emission spectral band $λ_{em}$ toward a mirror 6.3, the latter reflecting the emission light 14 toward an emission-image sensor 16. This emission-image sensor 16 comprises a matrix-array photodetector 19 that is coupled to a focusing optical system 15.

When the emission light is fluorescence light, the emission spectral band is a fluorescence spectral band $λ_{fluo}$, the emission-image sensor 16 being a fluorescence-image sensor. In this case, preferably, the fluorescence-image sensor 16 includes a fluorescence filter 17 the passband of which is defined depending on the fluorescence spectral band $λ_{fluo}$. The function of this fluorescence filter is to prevent detection, by the fluorescence-image sensor, of optical radiation that is not representative of the fluorescence.

The matrix-array photodetectors 39 and 19, which respectively detect visible and emission light, are charge-coupled-device (CCD) or complementary-metal-oxide-semiconductor (CMOS) photodetectors, or even a bolometer, in particular in the case of fluorescence in a spectral band in the infrared.

The rangefinding-light sensor 26 includes a rangefinding photodetector 29 that is able to detect light radiation in the rangefinding spectral band $λ_d$. It may also comprise a rangefinding filter 27 the passband of which is defined depending on the rangefinding spectral band $λ_d$. The function of this rangefinding filter is to prevent detection of optical radiation that is not representative of the rangefinding light 24 reflected by the object. It may also comprise focusing optics 25, in particular when the rangefinding photodetector 29 is a matrix-array photodetector, this particular situation being detailed below.

Figure 4:
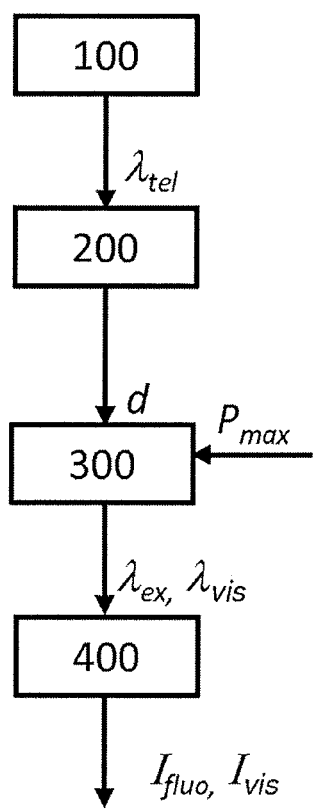
FIG. 4 shows the steps of a method according to the invention.

FIG. 4 summarizes the main steps of the method implemented in this example:

Step 100: a rangefinding beam 22 is emitted, in the form of a pulse, by the rangefinding-light source 21. This emission leads to the detection of this pulse by the triggering photodetector 23 and the activation of the rangefinding counter 53;

Step 200: rangefinding light 24 reflected by the object 10 is detected with the rangefinding sensor 26, this leading to the rangefinding counter 53 being stopped and the distance D travelled by the rangefinding light between the rangefinding source 21 and the rangefinding sensor 26 being determined;

Step 300: on the basis of this distance D, the distance d between the distal end 5 of the guide 2 and the object is determined, the excitation beam 12 emitted by the excitation source 11 being modulated depending thereon taking into account an illumination power $P_{max}$ that is acceptable to the object or a setpoint power $P_{ref}$;

Step 400: the excitation beam 12 is emitted with the excitation light source 11, and an emission image, for example a fluorescence image $I_{fluo}$, detected with the emission-image sensor 16. This step may also comprise the emission of visible light 32 with the visible-light source 31 and the detection of a visible image $I_{vis}$ with the visible-image sensor 36.

The use of transmitting optical fibers 4f, in the light guide 2, to direct the excitation beam 12 and the rangefinding beam 22 toward the object 10 is judged to be preferable to a configuration in which these beams are directed toward the object by the optical relay 4a. Specifically, in the latter configuration, which is illustrated in FIG. 1C, parasitic reflections may occur in the optical relay 4a, potentially causing untimely detection of the rangefinding light by the rangefinding sensor. Such an untimely detection would result in an erroneous distance measurement.

Generally, it is preferable for the optical paths followed by the excitation beam 12 and the rangefinding beam 22 to be different from those followed by the emission light 14 and the rangefinding light 24 that is reflected by the object.

Figure 5:
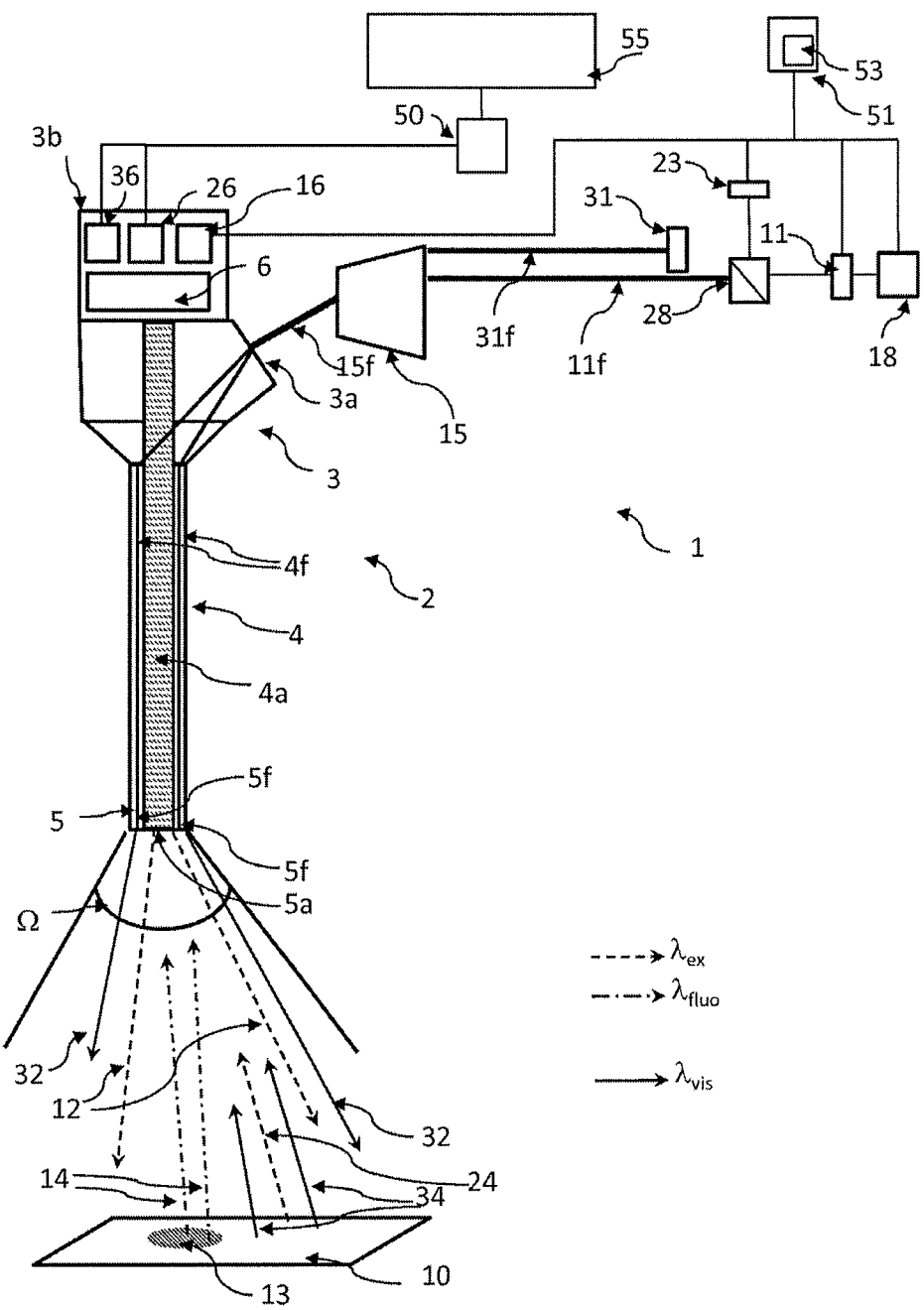
FIG. 5 shows a second embodiment of a device according to the invention.

FIG. 5 shows another embodiment, in which the excitation source 11 is pulsed and forms the rangefinding-light source 21. Thus, the rangefinding spectral band $\lambda_d$ corresponds to the excitation spectral band $\lambda_{ex}$. This limits the number of the light sources employed in the device. In such a configuration, the excitation-light source is preferably pulsed.

One portion of this beam is directed toward the triggering photodetector 23 by the distributer 28, this having the effect of activating the rangefinding counter 53. The other portion propagates toward the object 10 through the light guide 2. The object reflects some of the excitation beam and this excitation (or rangefinding) light 24 reflected by the object is transmitted to the rangefinding sensor 26.

Certain elements of the distance sensor may be integrated into the light guide, for example into the detecting module 3b of the proximal end 3.

Figure 6:
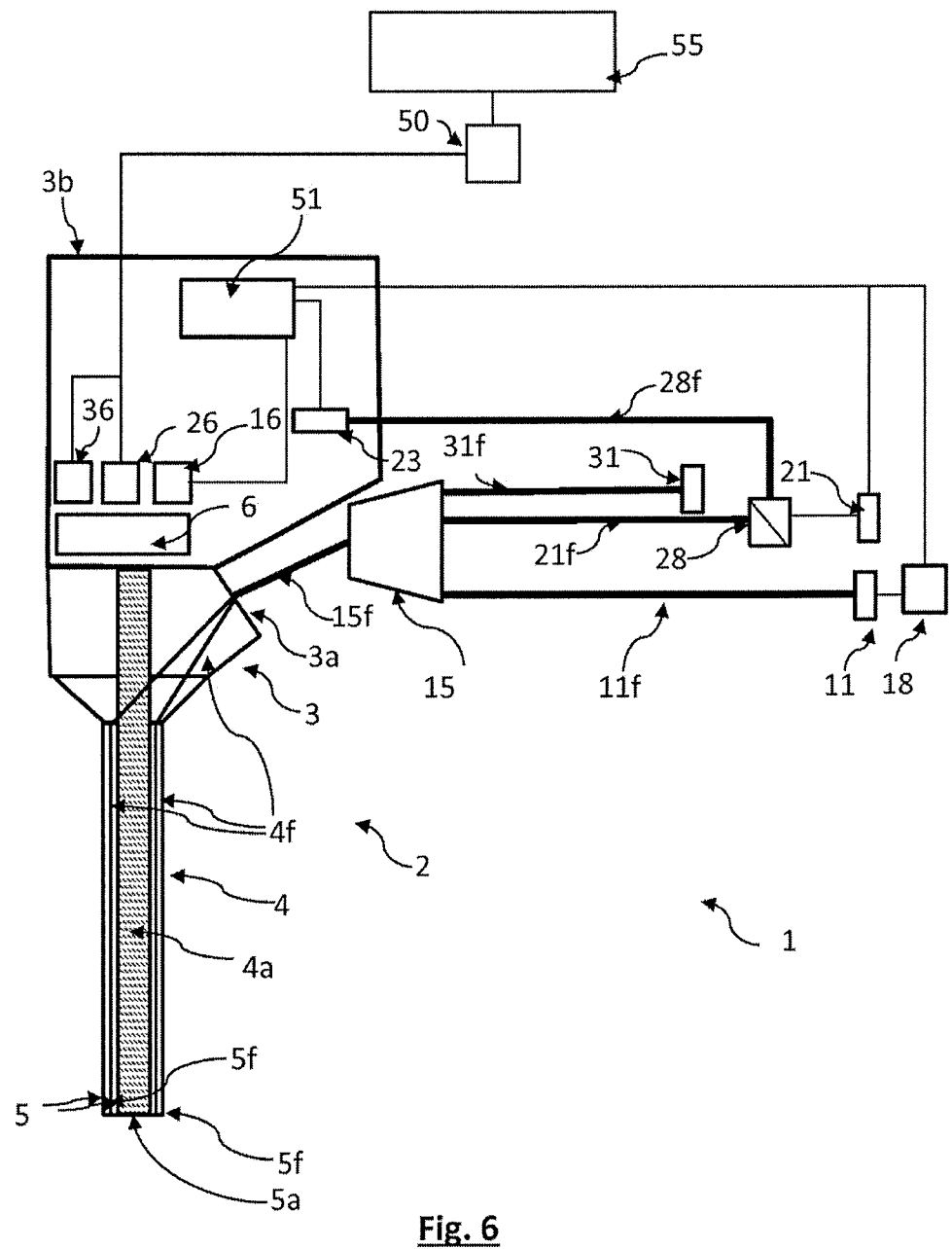
FIG. 6 shows one variant of the first or second embodiment of a device according to the invention.

FIG. 6 shows an example of such integration. In this figure, the triggering photodetector 23 is integrated into the detecting module 3b, just like the rangefinding processor 51. This assumes the distributer 28 and the triggering photodetector 23 are linked by an optical fiber 28f. This embodiment allows the length of the electrical connections between the key elements of the distance sensor, namely the triggering photodetector 23, the rangefinding sensor 26 and the rangefinding processor 51 to be decreased. This improves the precision of the measurement.

Figure 7:
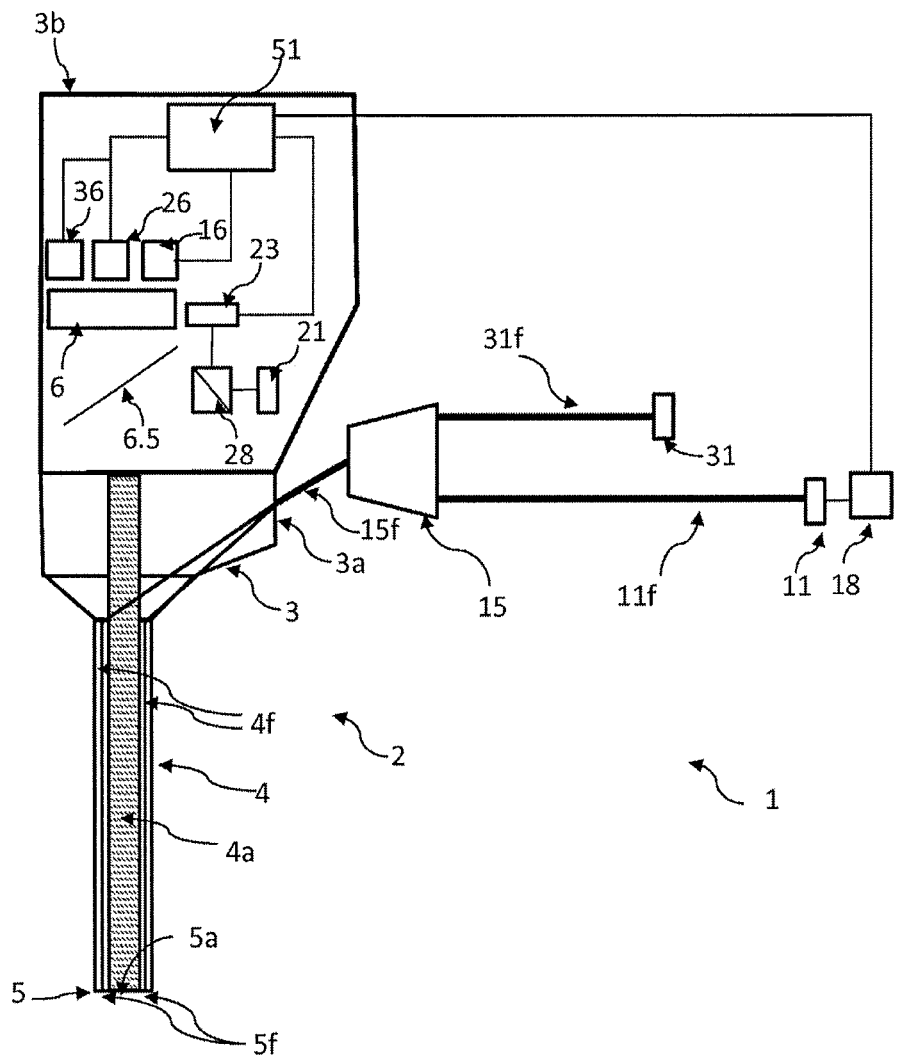
FIG. 7 shows another variant of the first or second embodiment of a device according to the invention.

According to another variant, shown in FIG. 7, the rangefinding-light source 21, the distributor 28, the triggering photodetector 23 and the processor are integrated into the detecting module 3b, forming part of the proximal end 3 of the light guide 2. A semi-reflective mirror 6.5 allows the rangefinding-light beam 22, produced by the rangefinding-light source 21 to be directed toward the distal end 5 of the light guide, through the relaying optical element 4a. This semi-reflective mirror also allows the emission light 14, or the rangefinding or visible light 24 or 34 reflected by the object 10, which light has propagated from the distal end 5, to be transmitted toward the spectral splitter 6. This variant allows complete integration of the distance-measuring sensor into the proximal end of the light guide 2. This allows a particularly compact device to be obtained.

Figure 8:
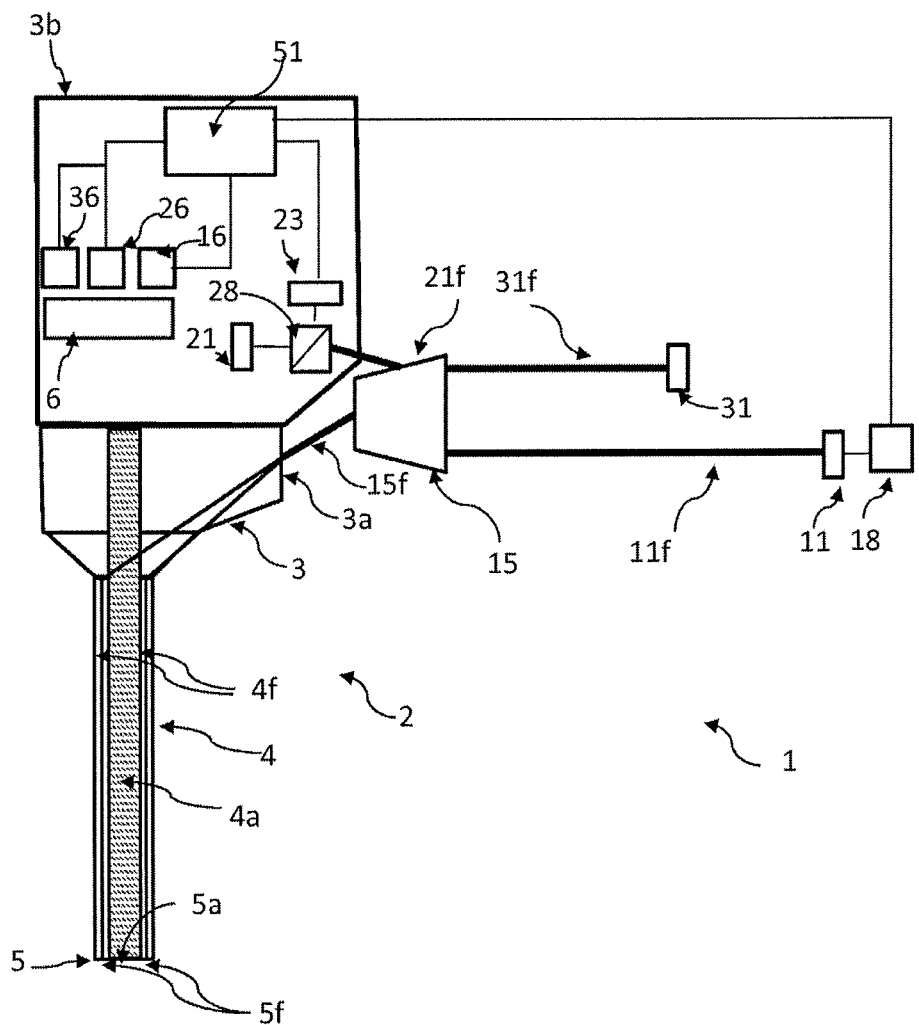
FIG. 8 shows another variant of the first or second embodiment of a device according to the invention.

The variant shown in FIG. 8 is similar to that shown in FIG. 7, the rangefinding beam 22 being transmitted between the rangefinding-light source 21 and the object 10 by excitation optical fibers 21f, coupling optical fibers 15f, and transmitting optical fibers 4f.

In the configurations shown in FIG. 7 or FIG. 8, the excitation source 11 may also be housed in the guide 2, in particular at its proximal end 3.

Figure 9:
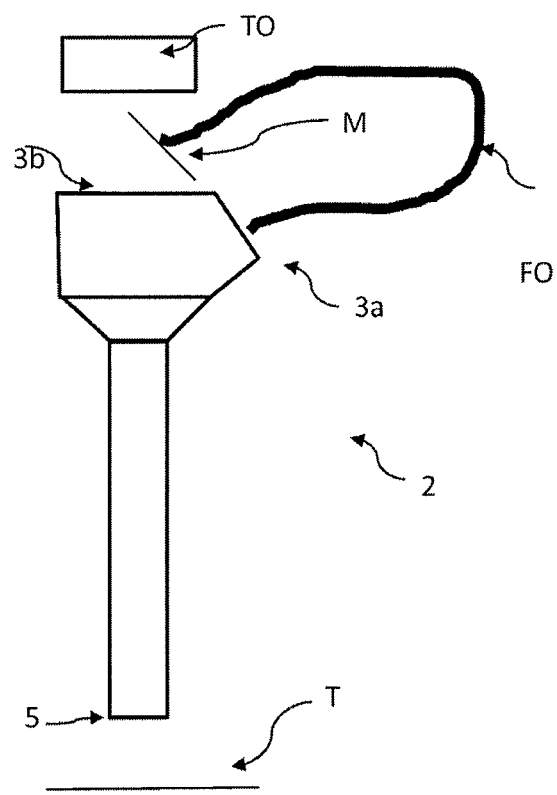
FIG. 9 shows an experimental setup.

An experimental trial was carried out using the device shown in FIG. 9. A commercial optical rangefinder TO was placed facing a mirror M, opposite which an optical fiber FO was placed, the latter being coupled to the entrance window 3a of a laparoscope 2. The rangefinder emitted a rangefinding-light beam that was able to be collected by the optical fiber FO and transmitted by the laparoscope to a target T. The optical rangefinder TO comprised a photodetector, the latter being placed facing the detecting module 3b of the laparoscope. The photodetector of the rangefinder detected the rangefinding light reflected by the target T and transmitted by the laparoscope. In this example, the detecting module consisted of a single transparent window. The length of the optical fiber FO was 2.5 mm.

Figure 10:
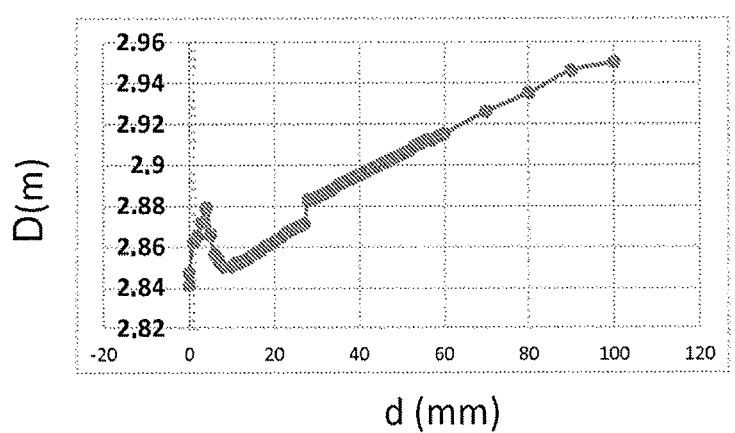
FIG. 10 shows the results of a trial carried out while implementing the experimental setup described in FIG. 9.

FIG. 10 shows the distance D measured by the rangefinder TO, corresponding to the optical path of the rangefinding-light beam, as a function of the distance d between the distal end 5 of the laparoscope 2 and the target T. This figure shows that the measurement of the measured distance D allowed the distance d to be estimated with precision provided that the distal end 5 of the laparoscope 2 was further than 15 mm from the object. The fluctuations that appeared when d<15 mm were due to nonuniform illumination of the target when the latter was placed too close to the distal end.

Figure 11:
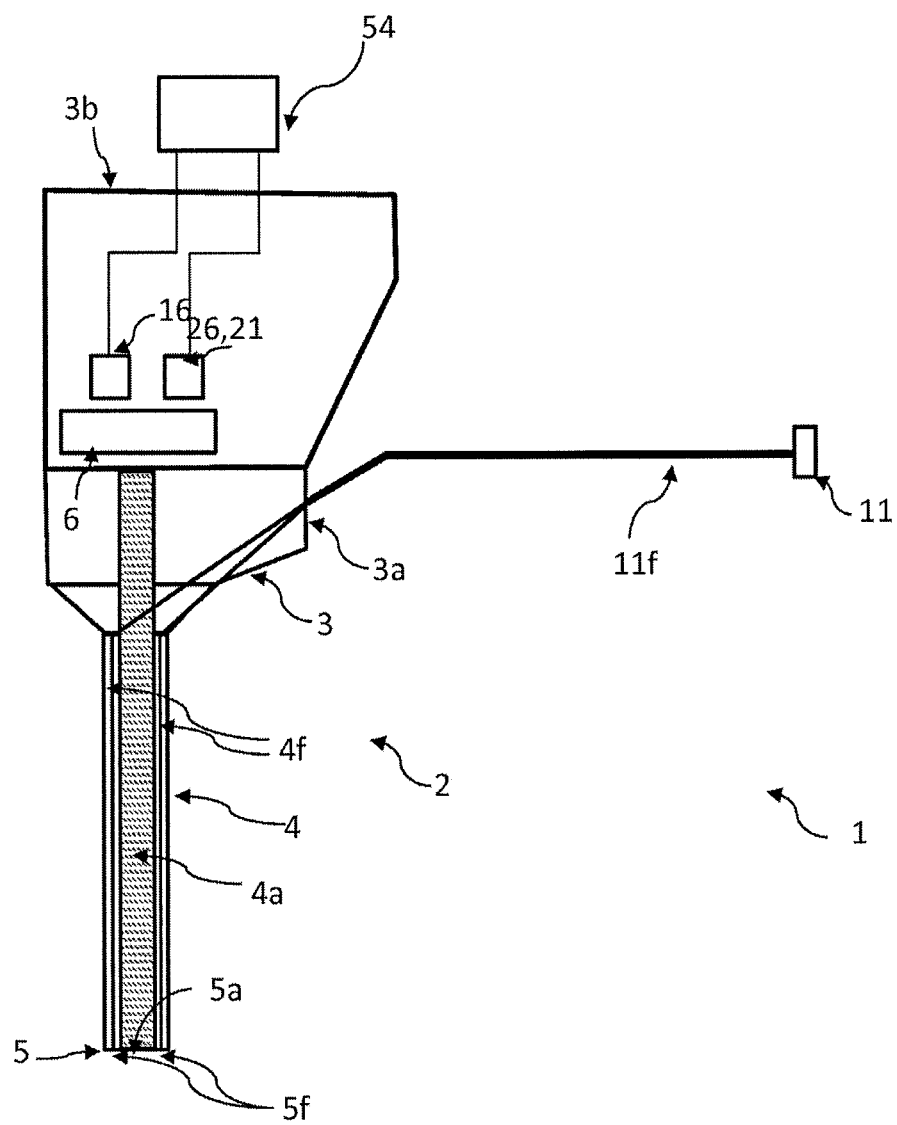
FIG. 11 shows a third embodiment of a device according to the invention.

FIG. 11 shows another embodiment in which the surface of the object is divided into a plurality of elementary surfaces. In this embodiment, it is not sought to establish the smallest distance between the distal end 5 of the light guide 2 and the surface of the object, as in the embodiments described above, but rather to obtain the distances between the distal end 5 and each surface element.

The rangefinding sensor 26 includes a matrix-array photodetector 29, each pixel of which is able to establish a measurement of the distance separating it from the surface element to which it is optically coupled, i.e. the surface element conjugated with this pixel. Such a photodetector may for example be a 3D time-of-flight video camera, for example the model SR4000 sold by Mesa Imaging.

Such a video camera includes a pulsed rangefinding-light source 21, for example taking the form of a light-emitting diode emitting in a spectral band $\lambda_d$ centered on the wavelength 850 nm. The rangefinding-light beam is directed toward the object 10 through the optical relay 4a, then the distal optical system 5a. The reflected rangefinding light is collected by the distal optical system 5a, then redirected toward the photodetector 29 through the optical relay 4a.

The photodetector is able to determine the time passed between the emission of the pulse of rangefinding light 22 by the light source and the detection of this pulse on each of these pixels. This allows a measurement of the distance travelled by the rangefinding light between the object and each pixel of the rangefinding-light sensor 26 to be obtained, from which it is possible to estimate the distance between the distal end 5 of the guide 2 and each surface element.

Such a device then allows a three-dimensional representation of the object 10 located facing the distal end 5 to be obtained.

This may allow tricky interventions, requiring precise information on the dimensions of the object, to be prepared or monitored. It may for example be a question of surgical interventions in which certain sensitive organs must not be touched by surgical instruments. The three-dimensional data relating to the examined bodily tissue may be transmitted to a haptic interface, in order to provide assistance with the surgical gesture, whether it be automated or manual. This haptic interface may in particular warn the surgeon when a surgical tool is located in proximity to a sensitive organ. Hence, the advantage of having three-dimensional data on the observed field available in real-time will be understood.

Preferably, the device shown in FIG. 11 includes an excitation-light source, such as described above, that is able to generate an excitation beam 12. The excitation beam is guided by the light guide 2 to the distal end 5. The emission light emitted by the object following this excitation is then collected by the distal optical system 5a and redirected toward the emission-image sensor 16. A processor 54 may allow three-dimensional data transmitted by the rangefinding-image sensor 26 and the image generated by the emission-image sensor 16 to be processed or displayed.

The excitation-light source 11 may be replaced by a visible-light source 31. Likewise, the emission-image sensor 16 may be replaced with a visible-image sensor 36. The device may in particular incorporate features of the devices presented in the preceding embodiments, provided that they are technically compatible.

Apart from laparoscopes, the invention is applicable to any endoscope or, generally, to any device for acquiring an image, in particular a fluorescence image, in response to a luminous excitation.

The invention claimed is:

1. A device for observing an object, comprising:
an excitation-light source configured to produce, in an excitation spectral band, an excitation beam that propagates toward the object;
a distance sensor including a rangefinding-light source configured to emit, in a rangefinding spectral band, a rangefinding beam that propagates toward the object, and including a rangefinding-light sensor configured to detect rangefinding light reflected, in the rangefinding spectral band, by the object;
a light guide configured to project the excitation beam and the rangefinding beam toward the object, in a single projection solid angle so as to form an illuminated field, the illuminated field corresponding to an intersection of said projection solid angle with the object;
an emission-image sensor configured to collect emission light emitted, in an emission spectral band, by the object under effect of the excitation beam, the emission-image sensor configured to acquire an emission image based on the collected emission light, the emission image corresponding to a distribution of emission light within the illuminated field;
the distance sensor configured to measure, based on a duration between the emission of the rangefinding beam by the rangefinding-light source and the detection, by the rangefinding-light sensor, of the rangefinding light reflected by the object, a smallest distance between a distal end of the light guide and the object within the illuminated field, the smallest distance corresponding to the distance between the distal end of the light guide and a point of the surface of the object said point being the closest point, within the illuminated field, to said distal end of the light guide; and
a modulator configured to adjust, based on the measured smallest distance between the distal end of the light guide and the object, a power of the excitation beam such that a power delivered by the excitation beam to the object as the light guide moves with relation to the object is below a predetermined maximum permitted power to avoid drying or burning the object.

2. The device as claimed in claim 1, wherein the light guide extends between a proximal end and the distal end, the light guide configured to transmit:
the excitation beam and the rangefinding beam toward the distal end; and
the emission light and the rangefinding light reflected by the object from the distal end to the proximal end;
the distal end of the light guide projecting the excitation beam and the rangefinding beam toward the object.

3. The device as claimed in claim 2, wherein the light guide includes, at the distal end, an optical system configured to collect the emission light and rangefinding light coming from the object, to direct the rangefinding light and the emission light coming from the object toward the proximal end of the light guide.

4. The device as claimed in claim 3, wherein the optical system is configured to direct the excitation beam and the rangefinding beam toward the object.

5. The device as claimed in claim 2, wherein:
the light guide includes transmitting optical fibers extending between the proximal end and the distal end of the light guide, said transmitting optical fibers being configured to guide the excitation beam and the rangefinding beam between the proximal end and the distal end, the end of each transmitting optical fiber at the distal end transmitting the excitation beam and the rangefinding beam toward the object.

6. The device as claimed in claim 2, wherein the light guide includes a spectral splitter configured to direct:
the emission light toward the emission-image sensor; and
the rangefinding light reflected by the object toward the rangefinding-light sensor.

7. The device as claimed in claim 2, further comprising:
a visible-light source configured to emit, in a visible spectral band, a visible-light beam toward the object; and
a visible-image sensor configured to collect visible light reflected by the object under an effect of illumination by the visible-light beam, the visible-image sensor configured to acquire a visible image based on the collected visible light,
wherein the light guide is configured to transmit:
the visible-light beam from the proximal end to the distal end; and
the visible light reflected by the object from the distal end to the proximal end.

8. The device as claimed in claim 2, wherein the rangefinding-light source and the excitation-light source are one and the same.

9. The device as claimed in claim 1, wherein the rangefinding spectral band is different from the excitation spectral band and from the emission spectral band.

10. The device as claimed in claim 1, wherein the distance sensor includes:
- a distributor configured to redirect a portion of the rangefinding beam emitted by the rangefinding-light source toward a triggering photodetector, the triggering photodetector configured to detect the portion of the rangefinding beam redirected by the distributor; and
- a rangefinding processor configured to determine a distance travelled by the rangefinding beam between the rangefinding-light source and the rangefinding-light sensor based on a trigger time at which the triggering photodetector detects the rangefinding beam and of an end time at which the rangefinding-light sensor detects the rangefinding light reflected by the object,
- the rangefinding processor configured to determine the smallest distance between the distal end of the light guide and the object based on the distance travelled by the rangefinding beam.

11. The device as claimed in claim 10, wherein the triggering photodetector and the rangefinding processor are included in the light guide.

12. The device as claimed in claim 1, wherein the illuminated field is larger than 5 mm$^2$ or larger than 1 cm$^2$.

13. The device as claimed in claim 1, wherein the light guide is rigid.

14. The device as claimed in claim 1, wherein the light guide is flexible.

15. The device as claimed in claim 5, wherein
- the light guide comprises a central segment that extends between the distal end and the proximal end, the central segment being configured to transfer an image between the distal end and the proximal end, and
- the transmitting optical fibers are distributed around the central segment.

16. The device as claimed in claim 15, wherein the central segment comprises relaying lenses or the transmitting optical fibers including a bundle of optical fibers.

17. A method for observing an object, comprising:
- illuminating the object with a rangefinding beam emitted, in a rangefinding spectral band, by a rangefinding-light source, the rangefinding beam being projected onto the object by a light guide in a single projection solid angle;
- illuminating the object using an excitation beam emitted, in an excitation spectral band, by an excitation-light source, the excitation beam being projected onto the object by the light guide in the single projection solid angle so as to form an illuminated field, the illuminated field corresponding to an intersection of said single projection solid angle with the object;
- detecting, by a rangefinding-light sensor, rangefinding light reflected, in the rangefinding spectral band, by the object;
- measuring a smallest distance between a distal end of the light guide and the object within the projection solid angle the illuminated field, based on a duration between the emission of the rangefinding beam and the detection of the rangefinding light reflected by the object, the smallest distance corresponding to a distance between the distal end of the light guide and a point of the surface of the object said point being the closest point, within the illuminated field, to said distal end of the light guide;
- providing the measured smallest distance to a modulator;
- collecting emission light emitted, by an emission-image sensor, in an emission spectral band, by the object under effect of the excitation beam, the emission-image sensor configured to acquire an emission image based on the collected emission light, the emission image corresponding to a distribution of emission light within the illuminated field; and
- adjusting, by the modulator, a power of the excitation beam based on the measured smallest distance between the distal end of the light guide and the object, such that a power delivered by the excitation beam to the object as the light guide moves with relation to the object is below a predetermined maximum permitted power to avoid drying or burning the object.

18. The method as claimed in claim 17, wherein
- the emission light is fluorescence light, and
- the emission light spectral band is a fluorescence spectral band that is different from the excitation spectral band.

19. The method as claimed in claim 17, wherein the rangefinding-light source and the excitation-light source are one and the same, the rangefinding spectral band corresponding to the excitation spectral band.

20. The method as claimed in claim 17, wherein the rangefinding spectral band is different from the excitation spectral band and from an emission spectral band.

21. The method as claimed in claim 17, wherein the emission light emitted by the object and the rangefinding light reflected by the object are collected by an optical system that is located at the distal end of the light guide, to direct the rangefinding light and the emission light coming from the object toward the emission-image sensor and the rangefinding-light sensor.

22. The method as claimed in claim 21, wherein the excitation beam and the rangefinding beam are projected onto the object by the optical system.

23. The method as claimed in claim 17, wherein:
- the excitation beam and the rangefinding beam are transmitted to the object by the light guide the distal end of which is placed facing the object,
- the light guide further configured to transmit the emission light emitted by the object and the rangefinding light reflected by the object to the emission-image sensor and the rangefinding-light sensor, respectively.

24. The method as claimed in claim 23, wherein
- the light guide includes transmitting optical fibers extending between the proximal end and the distal end of the light guide, and
- the excitation beam and the rangefinding beam are projected onto the object by the transmitting optical fibers extending between a proximal end and the distal end of the light guide.

25. The method as claimed in claim 24, further comprising:
- illuminating, through the light guide, the object with a visible-light beam emitted in a visible spectral band, by a visible-light source; and
- acquiring a visible image of the object using a visible-image sensor detecting visible light reflected by the object through the distal end to the proximal end of the light guide.

* * * * *

UNITED STATES PATENT AND TRADEMARK OFFICE
CERTIFICATE OF CORRECTION

| | |
|---|---|
| PATENT NO. | : 11,723,526 B2 |
| APPLICATION NO. | : 15/573372 |
| DATED | : August 15, 2023 |
| INVENTOR(S) | : Philippe Rizo |

It is certified that error appears in the above-identified patent and that said Letters Patent is hereby corrected as shown below:

In the Claims

In Column 19, Claim 17, Lines 57-58, delete "the projection solid angle the" and insert -- the --, therefor.

Signed and Sealed this
Second Day of January, 2024

Katherine Kelly Vidal
*Director of the United States Patent and Trademark Office*